United States Patent
Lewis

(10) Patent No.: US 7,062,015 B2
(45) Date of Patent: Jun. 13, 2006

(54) METHOD AND APPARATUS FOR OBTAINING SIMULTANEOUSLY ABSORPTION AND REFRACTION IMAGES BY USE OF A MONOCHROMATOR WITH INTEGRATED RADIATION DETECTOR

(75) Inventor: Robert Lewis, Warrington (GB)

(73) Assignee: Council for the Central Laboratory of the Research Councils, Warrington (GB)

(*) Notice: Subject to any disclaimer, the term of this patent is extended or adjusted under 35 U.S.C. 154(b) by 0 days.

(21) Appl. No.: 10/495,613

(22) PCT Filed: Oct. 28, 2002

(86) PCT No.: PCT/GB02/04851

§ 371 (c)(1),
(2), (4) Date: Nov. 12, 2004

(87) PCT Pub. No.: WO03/043498

PCT Pub. Date: May 30, 2003

(65) Prior Publication Data

US 2005/0069085 A1 Mar. 31, 2005

(51) Int. Cl.
*G01N 23/20* (2006.01)
*G21K 1/06* (2006.01)
*G01T 1/36* (2006.01)

(52) U.S. Cl. .............................. 378/84; 378/70; 378/82

(58) Field of Classification Search .................. 378/84, 378/71, 82, 85
See application file for complete search history.

(56) References Cited

U.S. PATENT DOCUMENTS

| 5,008,908 A | 4/1991 | Jach et al. |
| 5,850,425 A | 12/1998 | Wilkins |
| 5,987,095 A | 11/1999 | Chapman et al. |
| 6,041,098 A * | 3/2000 | Touryanski et al. ........... 378/70 |
| 6,353,656 B1 * | 3/2002 | LeVert et al. ................. 378/72 |
| 6,934,359 B1 * | 8/2005 | Chen et al. ................... 378/84 |
| 2004/0151278 A1 * | 8/2004 | Yokhin et al. ................. 378/84 |

OTHER PUBLICATIONS

Jach et al., "An X-Ray Monochromator Crystal which Detects the Bragg Condition," Nuclear Instruments and Methods in Physics Research, A263 (1988), 522-524.
Chapman et al., "Diffraction Enhanced X-Ray Imaging," Phys. Med. Biol., 42 (1997), 2015-2025.

* cited by examiner

*Primary Examiner*—Edward J. Glick
*Assistant Examiner*—Mona Sanei
(74) *Attorney, Agent, or Firm*—Michael Best & Friedrich LLP

(57) ABSTRACT

Apparatus for imaging an object (13) irradiated with an X-ray beam (12) by detecting a transmitted X-ray beam transmitted through the object. A crystal analyser (15) receives the transmitted X-ray beam and emits a first diffracted X-ray beam to a detector assembly (14) comprising first and second X-ray detectors (16 and 17). The first detector (16) is a monochromating semiconductor detector which detects a first portion of the first diffracted X-ray beam to generate first image data, and which diffracts a second portion of the first diffracted beam to the second detector (17) which generates second image data. Image processing means (18) are provided for combining the first and second image data to derive a refraction image and an absorption image of the object (13).

15 Claims, 3 Drawing Sheets

METHOD AND APPARATUS FOR OBTAINING SIMULTANEOUSLY ABSORPTION AND REFRACTION IMAGES BY USE OF A MONOCHROMATOR WITH INTEGRATED RADIATION DETECTOR

The present invention relates to an imaging method and apparatus. More particularly, the invention relates to X-ray imaging.

X-ray imaging systems are well known and are widely used in the medical field and in other applications such as non-destructive testing of mechanical structures. In a conventional X-ray imaging system an object is illuminated with X-rays which pass through the object with a degree of absorption dependent upon the density with respect to X-rays of the material of the object. Thus, a conventional X-ray image of a bone fracture for instance is effectively a shadow cast by the relatively dense bone within less dense surrounding tissue. Whilst such images are adequate for distinguishing between regions with significantly different density, the contrast is not sufficient to distinguish regions of similar density, such as tumas within healthy tissue etc.

Scanning X-ray imaging systems improve on the basic systems mentioned above by scanning the object with a fan shaped beam of X-rays. The X-ray source and an appropriate detector are simultaneously scanned to produce a series of lines of data, each representing the projected density of the object as a function of the position of the beam. The data can then be processed in a computer using standard mathematical techniques to recover a two dimensional image. Images with good levels of contrast can be obtained in this way, particularly if a monoenergetic X-ray beam is used. Such scanning techniques have been used to produce images with excellent density resolution enabling good differentiation between tissues with similar X-ray transmittance, for instance in the detection of tumas. Such systems have for example had significant impact on the early diagnosis of breast cancer.

More recently, X-ray imaging techniques have been improved still further by the development of diffraction enhanced X-ray imaging. U.S. Pat. No. 5,997,095 discloses such a system which makes it possible to produce images of exceptional quality that ire substantially free from scattering effects and moreover can produce images which are independently sensitive to refraction and absorption effects within the object being imaged. Separate refraction and absorption images provide different useful information. For instance, refraction images are very useful in highlighting boundaries or edges in heterogeneous regions within an object.

A crystal analyser (either Bragg or Laue type) is placed in the beam path between the object and an image plate or other detector to reflect the X-ray beam to the detector. The reflection is due to the diffraction of the X-ray beam by the crystal lattice, the reflectivity of the crystal being a strong function of the incident angle of the X-ray beam. Because the analyser crystal has only a narrow angular acceptance (referred to as the "rocking curve" of the crystal) scattering effects are almost entirely eliminated which greatly improves contrast. Separate refraction and absorption images are obtained by taking two independent images with the crystal analyser set to two different orientations with respect to the X-ray beam, corresponding to points on either side of the crystal rocking curve, and combining the data from these two images using relatively straight forward mathematical techniques. This process is described in more detail in the description below.

Whilst producing images of far superior contrast to conventional X-ray images, and providing information not available from conventional imaging systems, the prior art diffraction enhanced imaging system does suffer several drawbacks. If the refractive and absorption effects are to be separated it is necessary to take two independent images of the object. This increases the time taken to scan the object, and increases the X-ray dose to which the object is subjected. This is a particular disadvantage where the object being imaged is a part of the human body. In addition, for the data from the two images to be accurately combined there must be no movement or change in the object between the two image exposures, so that corresponding regions of each image cart be accurately correlated. This is again particularly problematical where the object is part of the human body, for instance if the system is to be used for mammography.

It is an object of the present invention to obviate or mitigate the above disadvantages.

According to a first aspect of the present invention there is provided apparatus for imaging an object irradiated with an X-ray beam by detecting a transmitted X-ray beam transmitted through the object, the apparatus comprising:

a crystal analyser for receiving the transmitted X-ray beam and emitting a first diffracted X-ray beam to a detector assembly comprising first and second X-ray detectors, wherein the first detector is a monochromating semiconductor detector which detects a first portion of the first diffracted X-ray beam to generate first image data, and which diffracts a second portion of the first diffracted beam to the second detector which generates second image data, and image processing means are provided for combining the first and second image data to derive a refraction image and an absorption image of the object.

According to a second aspect of the present invention there is provided a method of imaging an object, the method:

transmitting an X-ray beam through the object;

directing the transmitted X-ray beam at a crystal analyser to produce a first diffracted X-ray beam;

directing the first diffracted X-ray beam at a first detector comprising a monochromating semiconductor detector at an angle of incidence lying on the rocking curve of the detector;

directing a second diffracted beam emitted by the first detector to a second detector;

deriving first image data from X-rays detected at the first detector and second image data from X-rays detected at the second detector; and combining the first and second image data to derive a refraction image and an absorption image of the object:

Specific embodiments of the present invention will now be described, by way of example only, with reference to the accompanying drawings, in which.

Figure 1:
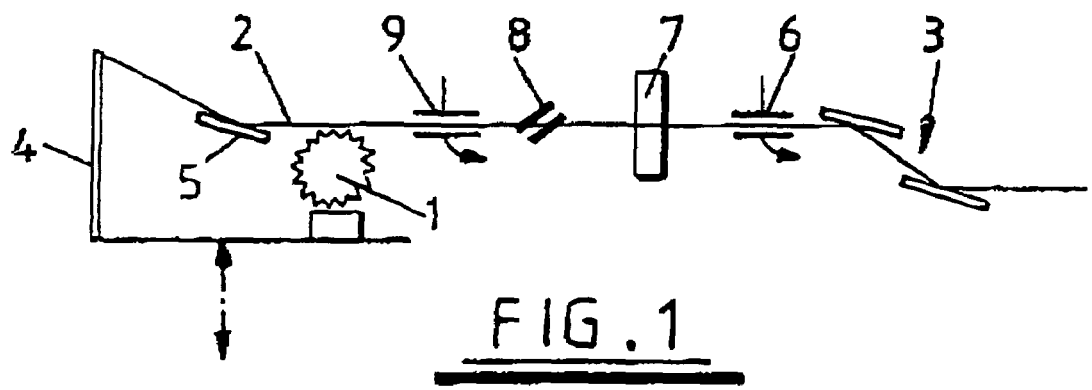
FIG. 1 is a schematic illustration of a prior art diffraction enhanced imaging system.

FIG. 1 illustrates one embodiment of the prior art diffraction enhanced imaging system of U.S. Pat. No. 5,987,095 mentioned above. An object 1 is scanned with a monoenergetic X-ray beam 2, generated by a double crystal monochromator 3 from a synchrotron source, to provide an image on an image plate 4 (or other suitable detector) via a crystal analyser 5.

The double crystal monochromator 3 may be of a known type, for instance constructed of silicon with a (3,3,3) lattice plane structure to produce an X-ray beam 2 of approximately 18 KeV and a band width of 1.5 eV, and of the order of 80 mm wide and 0.1 mm high. An ionisation chamber 6 is included to monitor tuning of the monochromator 3 and an absorber 7 is provided to enable control of the X-ray dose. A shutter 8 (for instance a rotary shutter) is used to control image exposure and a further ionisation chamber 9 positioned in the beam path between the shutter 8 and the object 1 is provided to monitor X-ray dose at the surface of the object 1.

The X-ray beam transmitted through the object is reflected on to the image plate 4 by the crystal analyser 5 (which in this embodiment is a Brags type analyser) orientated to diffract the beam in the vertical plane. Precise angular orientation of the crystal analyser 5 relative to the transmitted X-ray beam direction is controlled by a stepper motor driven by a translation stage (not shown). The reflected image is sensitive to refractive effects in the body 1 because the reflected intensity is a steep function of the angle of incidence of the X-ray beam at the crystal surface (which as mentioned above is referred to as the rocking curve of the crystal). The crystal analyser 5 may take a variety of forms but preferably has a lattice structure matched to the monochromator crystals 3 (the analyser crystal may itself be regarded as a monochromator).

Figure 2:
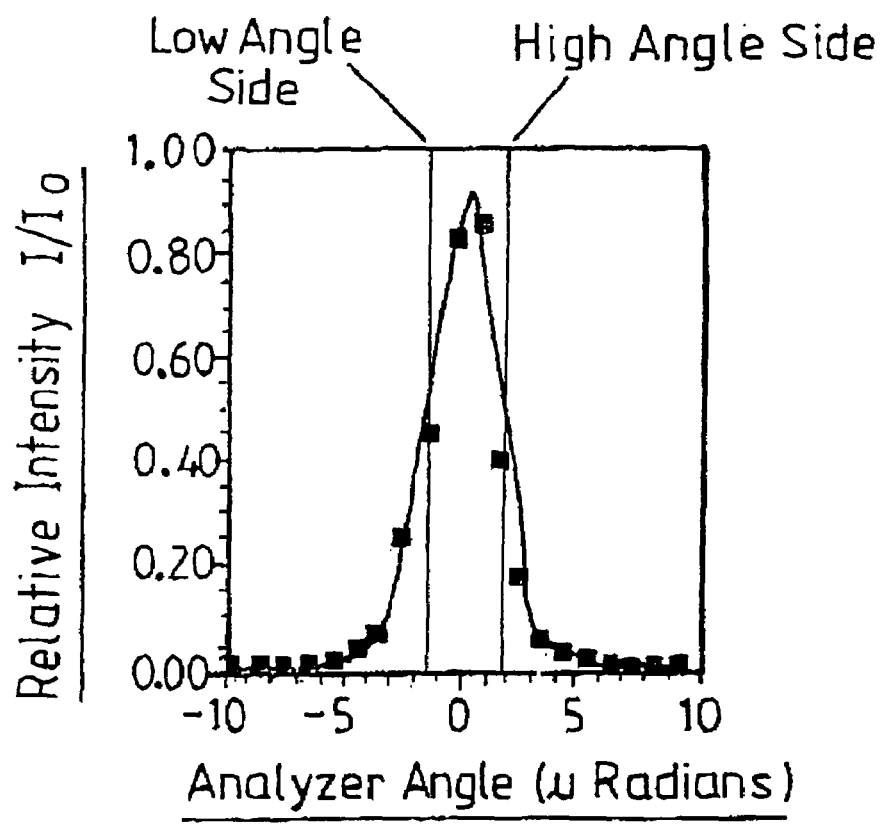
FIG. 2 illustrates the rocking curve of a typical analyser crystal used in a diffraction enhanced imaging system.

The rocking curve for a silicon analyser crystal with a (3,3,3) lattice structure at an X-ray imager level of 18 KeV is shown in FIG. 2. This shows the intensity (relative to the maximum reflective intensity) of the crystal with variations of angle about the Bragg angle at which the intensity is maximum (which corresponds to the 0 degree position indicated in FIG. 2). As will be appreciated from FIG. 2, only X-rays aligned within a few µradians of the transmitted beam will be reflected. Since scattering angles due to diffraction effects within the body (small-angle scattering) are typically of the order of a few milliradians, most of the diffraction scattering is eliminated from the image. Refraction effects on the other hand, which are due to spatial variations in the density and/or thickness of the material along the direction of transmittance of the X-ray beam will generally be less than about 2 µradians, (and typically less than 1 µradian) and are therefore reflected Similarly, other coherent and incoherent scattered components of the beam will be eliminated from the reflected beam by the analyser crystal, so that that portion of the transmitted X-ray beam that arrives at the detector (designated $I_R$) has been affected by refraction and attenuation due to absorption and extinction only.

Any single image produced on the image plate 4 would be a combined absorption and refraction image almost entirely free of scattering effects. Although this in itself provides an improvement in contrast over conventional X-ray images, the most significant improvement is obtained by taking two independent images with the crystal analyser 5 at different orientations corresponding to different points on the rocking cures, which are then combined to derive separate refraction and absorption images. Thus, a first image is taken by scanning the object (which involves simultaneously moving the image plate 4 and object 1) with the analyser crystal orientated so that the transmitted direction of the X-ray beam is incident on the crystal at an angle lying on one side of the rocking curve. Preferably the selected angle is half the Darwin width (the Darwin width being the full width at half maximum of the curve) at which point the gradient of the curve is steepest. The first image is stored and second image is scanned after first adjusting the orientation of the crystal analyser to correspond with a point on the opposite side of the rocking curve to that used for the first image (again preferably at half the Darwin width). The two images are then compared and combined to separate out the diffraction and absorption information to generate independent refraction and absorption images.

The combination is preferably done by first digitising the images and then comparing the image data on a pixel by pixel basis using an appropriate algorithm. Pixels from each image corresponding to the same region of the object must be aligned with one another so it is important that the object does not change or move between exposure of the two images.

The mathematical processing required to separate the refraction and absorption images is relatively straight forward. Since the analyser crystal orientation is chosen to diffract the beam in the vertical plane, it is sensitive only to the vertical component, $\Delta\theta_z$, of the refracted X-rays. If the analyser crystal is set to a relative angle $\theta$ from the Bragg angle $\theta_B$ where $\theta_B+\theta$ is the angle between the incident transmitted X-ray beam and the crystal diffraction planes, the intensity of the reflected beam ($I_B$) is given by:

$$I_B = R(\theta_B + \theta)$$

Where $R(\theta)$ is the analyser reflectivity (relative to the peak reflectivity) and $I_R$ is the intensity of the portion of the transmitted X-ray beam which has only been affected by refraction and attenuated by absorption and extinction.

As mentioned above the analyser is preferably set to $\theta = +/- \Delta\theta_D/2$ (where $\Delta\theta_D$ is the Darwin width) respectively for the two images. Thus for an incident X-ray which is not deviated as it passes through the object, and is therefore incident on the angular crystal at $+/-\Delta\theta_D/2$, the analyser reflectivity will be 0.5. For an X-ray refracted within the object by $\Delta\theta_z$, the reflected intensity will be:

$$I_B = I_R r \left[ \theta_B \pm \frac{\Delta\theta_D}{2} + \Delta\theta_z \right]$$

The reflected intensity of any refracted X-rays will vary due to the slope of the rocking curve. For instance, for the image taken with the crystal analyser orientated at $\Delta\theta_D/2$ positive (i.e. on the high—angle side of the rocking curve) any X-rays refracted with $\Delta\theta_z>0$ will be diffracted by the analyser with a reflectivity <0.5. On the other hand any X-rays refracted with $\Delta\theta_z<0$ will be diffracted by the analyser crystal with a reflectivity >0.5. For the second image, with the analyser crystal orientated so that $\Delta\theta_D/2$ is negative, the effect is reversed since the derivative of the rocking curve $(dR/d\theta)$ is of the opposite sign.

If refracted components of the X-ray beam deviate more than $\Delta\theta_D 2$, the reflectivity will not be unique and refraction effects cannot be resolved. However, in practical tests refraction angles have been measured to be within about +/−0.2 µradians, so that all possible refraction angles lie within a limited region of the rocking curve. At such small angles of $\Delta\theta_z$, and given that at $+/-\Delta\theta_D/2$ the slope of the rocking curve is fairly constant, the analyser reflectivity can be expressed as a two-term Taylor series approximation:

$$R(\theta_B + \Delta\theta_Z) = r(\theta_B) + \frac{dR}{d\theta}(\theta_B)\Delta\theta_Z$$

The intensities of the reflected X-rays on the high-side and low-side of the rocking curve are therefore respectively:

$$I_L = I_R(R_L = \text{Grad}_L \cdot \Delta\theta_z)$$

$$I_H = I_R(R_H + \text{Grad}_H \cdot \Delta\theta_Z)$$

The above equations are simultaneous equations in which the two unknowns are $I_R$ and $\Delta\theta_z$, for which the solutions are simply:

$$I_R = \frac{(I_H \cdot \text{Grad}_L + \text{Grad}_H \cdot I_L)}{(-\text{Grad}_L \cdot R_H + \text{Grad}_H \cdot R_2)}$$

and $$\Delta\theta_z = \frac{(I_L \cdot R_H + R_L \cdot I_H)}{(-I_H \cdot \text{Grad}_L + \text{Grad}_H \cdot I_L)}$$

Data from corresponding regions of the two images can therefore be compared, and combined, to derive apparent absorption ($I_R$) and refraction ($\Delta\theta_Z$) information for each region of the object (for instance on a pixel-by-pixel basis) and that information used to construct two images, an absorption and a refraction image respectively.

Figure 3:
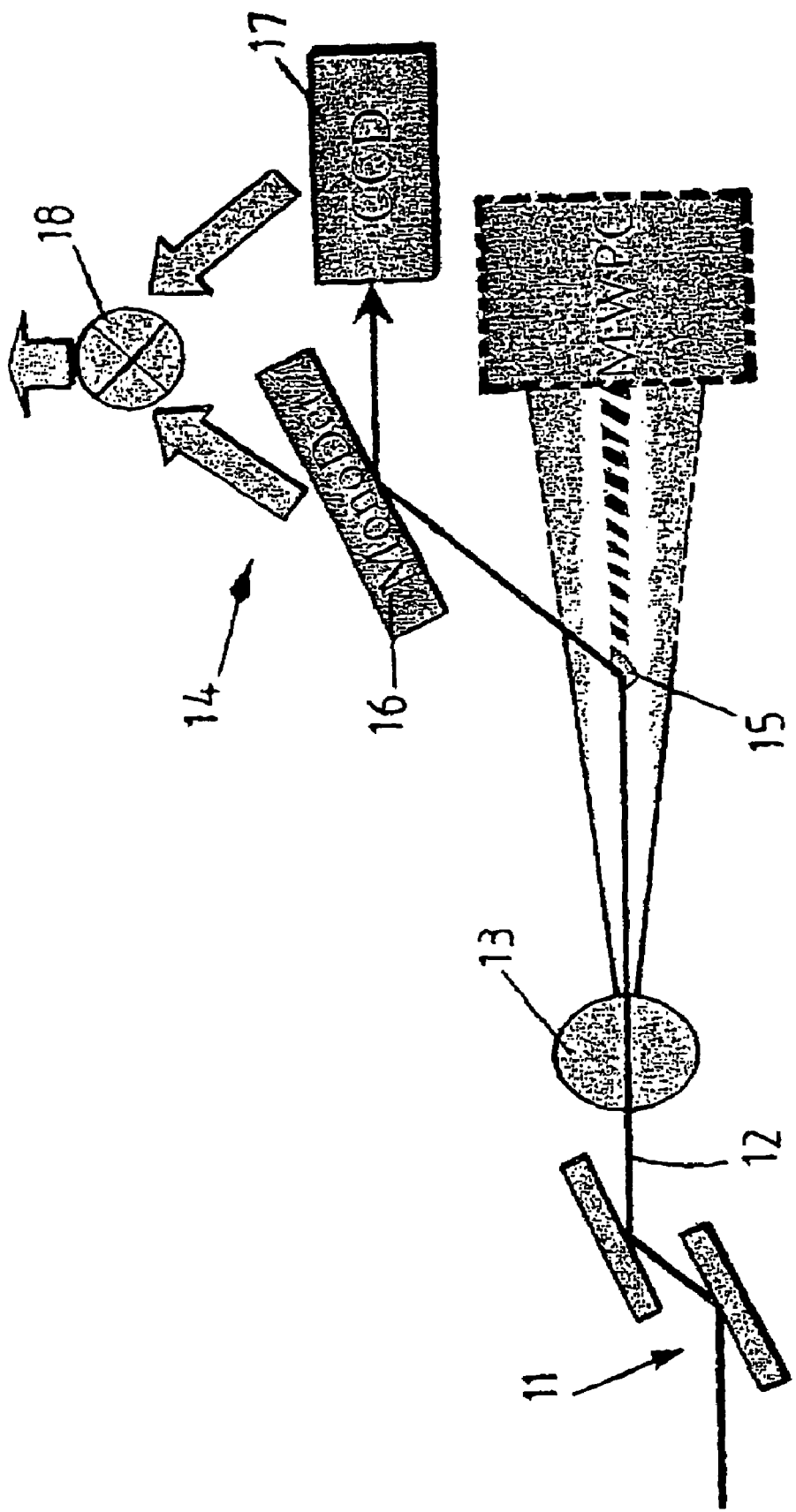
FIG. 3 is a schematic illustration of an imaging system in accordance with the present invention.

Referring now to FIG. 3, this is a schematic illustration of imaging apparatus according to the present invention. As with the apparatus of FIG. 1, a monochromator 11 is used to generate a monoenergetic X-ray beam 12 (derived from a synchrotron source) to scan an object 13. The transmitted X-ray beam is reflected to a detector arrangement 14 by analyser crystal 15 which eliminates scattering effects from the image in exactly the same way as analyser crystal 5 of the apparatus of FIG. 1. Details of the monocrhomator and analyser crystal may be exactly the same as disclosed in relation to the apparatus of FIG. 1. Other features, such as details of the shutter and X-ray beam control arrangements have been omitted from FIG. 3 for simplicity but similarly may be based on the components of the apparatus of FIG. 1.

The essential difference between the present invention and the prior art diffraction enhanced imaging system is that the detector arrangement of the present invention comprises first and second detectors 16 and 17 respectively which simultaneously record image data obviating the need to scan the object 13 twice. The image data detected at detectors 16 and 17 is combined at an image processing stage indicated by reference 18 to produce independent absorption and refraction images.

In more detail, the first detector 16 is a crystalline semi conductor detector which functions both as a detector and as a monochromator which reflects (Bragg reflection) components of the incident X-ray beam falling within its rocking curve to the second detector 17 which may be any conventional form of detector, such as a CCD device. Components of the X-ray beam not reflected by the first detector 16 are simply detected by the detector 16.

Semiconductor detectors having the basic structure suitable for use as the combined detector/monochromator are known and will not be described in detail here. For instance, some commercially available silicon strip detectors will have a good crystalline structure providing good reflection intensities within a narrow rocking curve. A method particularly suitable for producing detectors having the characteristics required by the present invention is disclosed in the article "An X-Ray monochromator that detects the Bragg condition"; T. Jach et al; Nuclear Instruments and Methods in Physics Research; A263 (1988) 522–524. This discloses how boron diffusion may be used to bury a diode structure some 0.6 microns beneath a silicon substrate surface. It also shows how the diode current drops off as the Bragg condition is met. The reflectivity of such a doped material differs very little from that of the raw material.

To maximise the intensity of the X-ray beam reaching the detector arrangement, the analyser crystal 15 is preferably set at the Bragg angle relative to the X-ray beam transmitted through the object (i.e. corresponding to the peak of its rocking curve). The detector 16 is however orientated with respect to the beam reflected from the analyser crystal 15 so that the incident radiation falls on one or other side of the rocking curve of the detector 16 so that only a portion of the incident X-ray beam is reflected on to detector 17. It does not matter which side of the rocking curve the detector crystal 16 is orientated to, but preferably the detector 16 is orientated at $\Delta\theta_L/2$ with respect to the X-ray being reflected from analyser crystal 15 for the reasons mentioned above in relation to the apparatus of FIG. 1.

The image data received at the second detector 17 therefore corresponds to the image data received at the detector 4 of the apparatus of FIG. 1 for a single image. Assuming the detector 16 is orientated on the lower-side of its rocking curve, the intensity of the beam reflected into detector 17 is simply $I_L$, which as above is given by expression:

$$I_L = I_R(R_L = \text{Grad}_L \cdot \Delta\theta_z)$$

The intensity ($I_M$) of the image data detected by the monochromating detecting crystal 16 will simply be the difference between the intensity of the X-ray beam reflected by analyser crystal 15 (i.e. $I_R$ assuming analyser 15 is set to the Bragg angle as mentioned above) and $I_L$. That is:

$$I_M = I_R - I_L$$

The above two equations are again two simple simultaneous equations for which the unknowns are $I_R$ and $\Delta\theta_Z$, with solutions:

$$I_R = I_M + I_L \tag{7}$$

and $$\Delta\theta_2 = \frac{(I_L + .R_L . I_M + R_L . I_L)}{(\text{Grad}_L(I_M . I_L))}$$

Thus, the image data from the two detectors can be combined in a similar manner to the image data from the two independent images of the prior art system (e.g. by digitising the data and combining this on a pixel-by-pixel basis) to produce independent absorption and refraction images of comparable contrast and resolution to those obtained from the prior art diffraction enhanced imaging system mentioned above.

Figure 4C:
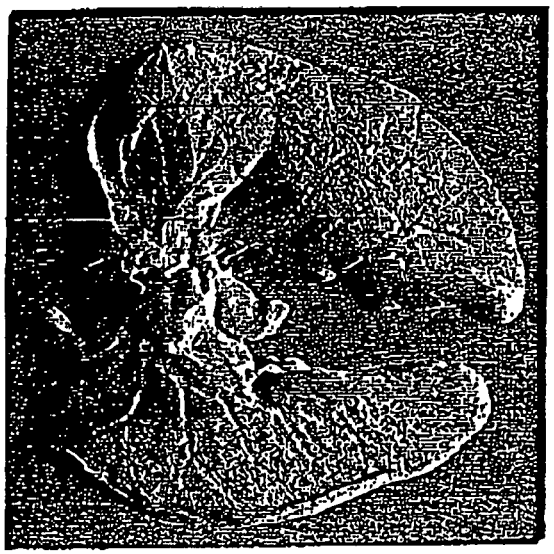
FIGS. 4a to 4c are images of a mouse lung which illustrate the effectiveness of the present invention in comparison with a conventional radiograph.
Figure 4B:
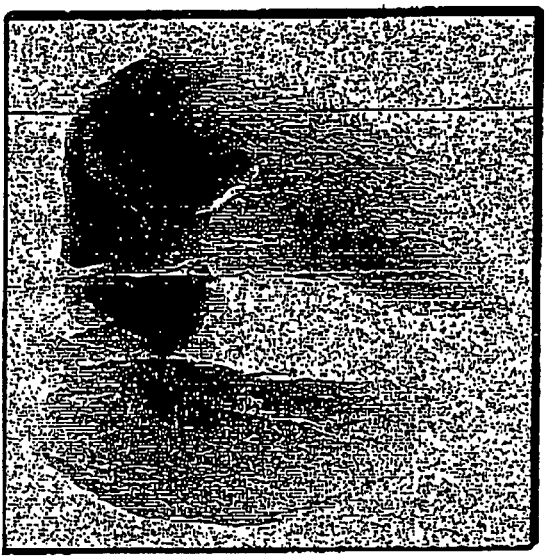
Figure 4A:
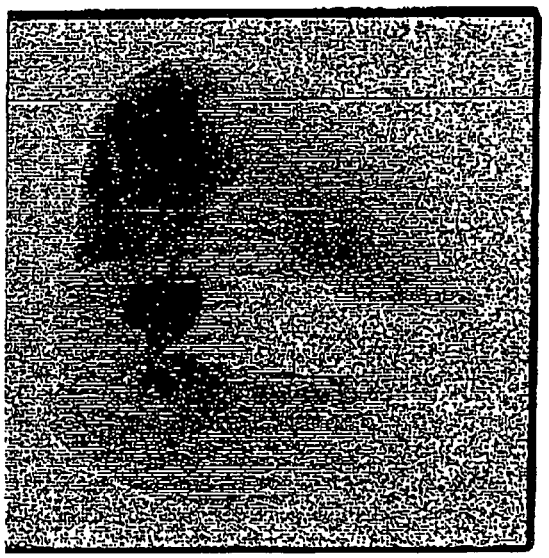

FIG. 4a to 4c show three X-ray images of a mouse lung. FIG. 4a is a conventional radiograph whereas FIGS. 4b and 4c are absorption and refraction images respectively obtained by apparatus in accordance with the present invention. The improvements in contrast are clearly visible. In addition, the three-dimensional shadowed appearance of the refraction image, arising because the contrast in the refraction images is a result of a refractive index gradience along the X-ray beam path, is also clearly visible.

The present invention has several important advantages over the prior art diffraction enhanced imaging system mentioned above. Since only a single exposure of the object is required, the two images necessary to derive the independent refraction and absorption data being obtained simultaneously, problems associated with any change or movement in the object between separate exposures are obviated. In addition, the overall X-ray dose is reduced which is particularly significant when imaging living tissue. Both of these advantages would be significant in, for instance, mammography. In addition, all of the transmitted beam (minus the scattering components removed by the analyser crystal) is used in deriving the images so that the beam intensity required to provide good images is reduced, again advantageously reducing the required X-ray dose.

The basic system of the present invention can be modified and enhanced in a number of conventional ways. As mentioned above, control features such as provision of ionisation chambers and absorbers which are included in prior art systems may similarly be included in the system of the present invention. In other words, apparatus components upstream of the analyser crystal 15 may be entirely conventional.

A Lane type analyser crystal may be used in place of the Bragg type analyser crystal 15 enabling the generation of a diffraction image on a third detector as indicated by chain dot in FIG. 3. This enables derivation of a third scatter image as described in U.S. Pat. No. 5,987,095 by combining the third image data with the absorption and refraction image data.

Similarly, as mentioned above, the detectors 16 and 17 may be conventional components. In particular, suitable monochromating semiconductor crystalline detectors which may be used as the combined monochromator/detector 15 are well known.

The image data analysis, and image production/display systems, which are required to derive the refraction and absorption images may also be entirely conventional, for instance as proposed for the prior art diffraction enhanced imaging system of U.S. Pat. No. 5,987,095. Other possibilities will be apparent to the skilled reader and thus no detailed discussion will be made of these systems here.

Control of the orientation of the monochromator/detector 16 may be achieved using conventional stepper motors as with the prior art. Similarly, systems for controlling the scanning movement of the object and detectors may be entirely conventional.

It will be appreciated that the present invention can be used to provide images in any application to which conventional X-ray imaging, or diffraction enhanced imaging, can be applied. This includes medical imaging and non-medical imaging, such as non-destructive testing of mechanical structures.

Other possible modifications and applications of the present invention will be readily apparent to the appropriately skilled person.

The invention claimed is:

1. Apparatus for imaging an object irradiated with an X-ray beam by detecting a transmitted X-ray beam transmitted through the object, the apparatus comprising:
a crystal analyser for receiving the transmitted X-ray beam and emitting a first diffracted X-ray beam to a detector assembly comprising first and second X-ray detectors, wherein the first detector is a monochromating semiconductor detector which detects a first portion of the first diffracted X-ray beam to generate first image data, and which diffracts a second portion of the first diffracted beam to the second detector which generates second image data, and image processing means are provided for combining the first and second image data to derive a refraction image and an absorption image of the object.

2. Apparatus according to claim 1, wherein the crystal analyser is orientated to maximise the intensity of the first diffracted beam.

3. Apparatus according to claim 1, wherein the crystal analyser is a Bragg or Laue analyser.

4. Apparatus according to claim 3, wherein the crystal analyser is a Bragg type analyser orientated at the Bragg reflection angle with respect to the transmitted X-ray beam.

5. Apparatus according to claim 3, wherein the analyser is a Laue type analyser which emits a forward diffracted X-ray beam in addition to said first diffracted X-ray beam, and further comprising a third detector to detect said forward diffracted X-ray beam and means for deriving a scatter image of the object by combining the first, second and third image data to remove refraction and absorption effects from the third image data.

6. Apparatus according to claim 1, wherein the first detector is orientated so that the first diffracted beam is incident at the first detector at an angle falling on one slope of the detectors rocking curve.

7. Apparatus according to claim 6, wherein the angle of orientation of the first detector relative to the first diffracted beam is $+/-\Delta\theta_D/2$ where $\Delta\theta_D$ is the full width at half maximum of the rocking curve of the detector.

8. Apparatus according to claim 1, wherein the first detector is a silicon strip detector.

9. Apparatus according to claim 1, wherein the first and second detectors are capable of producing first and second digitised images from said first and second image data.

10. Apparatus according to claim 1, wherein the first and second image data is combined by digitising the first and second image data and comparing and combining it on a pixel-by-pixel basis to form digitised refraction and absorption images.

11. Apparatus according to claim 10, wherein the digitised refraction and absorption images are converted to visual images.

12. Apparatus according to claim 1, wherein the second detector detects the intensity of the incident X-ray beam and the first detector detects the intensity of the first refracted beam minus the second diffracted beam, and said processing means combines the detected intensities for corresponding regions of the object to derive said absorption and refraction images.

13. Apparatus according to claim 1, further comprising means for generating a substantially monoenergetic X-ray beam and directing said X-ray beam at the object.

14. Apparatus according to claim 1, further comprising means for scanning the object with said X-ray beam.

15. A method of imaging an object, the method comprising:
transmitting an X-ray beam through the object;
directing the transmitted X-ray beam at a crystal analyser to produce a first diffracted X-ray beam;
directing the first diffracted X-ray beam at a first detector comprising a monochromating semiconductor detector at an angle of incidence lying on the rocking curve of the detector;
directing a second diffracted beam emitted by the first detector to a second detector;
deriving first image data from X-rays detected at the first detector and second image data from X-rays detected at the second detector; and
combining the first and second image data to derive a refraction image and an absorption image of the object.

* * * * *